United States Patent
Bitner et al.

(10) Patent No.: US 6,787,307 B1
(45) Date of Patent: Sep. 7, 2004

(54) LYSATE CLEARANCE AND NUCLEIC ACID ISOLATION USING SILANIZED SILICA MATRICES

(75) Inventors: Rex M. Bitner, Cedarburg, WI (US); Daniel J. Simpson, Middleton, WI (US); Roderick G. Flemming, McFarland, WI (US); Susan C. Koller, Verona, WI (US)

(73) Assignee: Promega Corporation, Madison, WI (US)

( * ) Notice: Subject to any disclaimer, the term of this patent is extended or adjusted under 35 U.S.C. 154(b) by 87 days.

(21) Appl. No.: 09/711,782

(22) Filed: Nov. 13, 2000

Related U.S. Application Data

(63) Continuation-in-part of application No. 09/475,958, filed on Dec. 30, 1999.
(60) Provisional application No. 60/134,156, filed on May 14, 1999.

(51) Int. Cl.[7] .......................... C12Q 1/68; C12Q 1/70; G01N 33/53
(52) U.S. Cl. ............................. 435/6; 435/5; 435/7.1; 435/7.2
(58) Field of Search .................. 435/6, 91, 803; 436/17; 536/27, 25.4, 18.4, 25.41

(56) References Cited

U.S. PATENT DOCUMENTS

| | | |
|---|---|---|
| 3,652,761 A | 3/1972 | Weetall |
| 4,233,169 A | 11/1980 | Beall et al. |

(List continued on next page.)

FOREIGN PATENT DOCUMENTS

| | | |
|---|---|---|
| CA | 2223821 | 12/1996 |
| DE | 39 35 098 a1 | 4/1991 |
| DE | 43 07 262 | 9/1994 |
| DE | 195 12 368 A1 | 10/1996 |
| EP | 0 741 141 A2 | 11/1996 |
| EP | 0 757 106 A2 | 2/1997 |
| EP | 0 875 271 A2 | 11/1998 |
| JP | 9-327290 | 12/1997 |
| JP | 9-327291 | 12/1997 |
| WO | WO 83/03363 | 10/1983 |
| WO | WO 91/12079 | 8/1991 |
| WO | WO 95/06652 | 3/1995 |
| WO | WO 96/31781 | 10/1996 |
| WO | WO 97/29825 | 8/1997 |
| WO | WO 98/31461 | 7/1998 |
| WO | WO 98/31840 | 7/1998 |
| WO | WO 00/69872 | 11/2000 |
| WO | WO 00/70040 | 11/2000 |

OTHER PUBLICATIONS

Anspach, "High–Performance Liquid Affinity Chromatography with Phenylboronic Acid, Benzamidine, Tri–L–alanine, and Concanavalin A Immobilized on 3–Isothiocyanatopropytriethoxysilane–Activated Nonporous Monodisperse Silicas", *Anal. Biochem* (1989) 179:171–181.

(List continued on next page.)

*Primary Examiner*—Jezia Riley
(74) *Attorney, Agent, or Firm*—Michael Best & Friedrich LLP; Grady J. Frenchick; Jill A. Fahrlander

(57) ABSTRACT

A method is provided for using a silanized silica matrix to isolate a target nucleic acids, such as plasmid DNA, fragments of DNA, chromosomal DNA, or RNA from contaminants, including proteins, lipids, cellular debris, or non-target nucleic acids. The silanized silica matrix comprises a silica based solid phase and a plurality of silane ligands covalently attached to the surface of the solid phase. Non-target material adsorbs to the silanized silica matrix in the presence of a sufficient concentration of chaotropic salt, while target nucleic acids adsorb to the matrix under other solution conditions. The method of using the silanized silica matrix of the present invention can be used to clear solutions of disrupted biological material, and to isolate nucleic acids therefrom or from other solutions containing nucleic acids and at least one contaminant.

51 Claims, 3 Drawing Sheets

U.S. PATENT DOCUMENTS

| | | | |
|---|---|---|---|
| 4,297,337 A | | 10/1981 | Mansfield et al. |
| 4,298,500 A | | 11/1981 | Abbott |
| 4,395,271 A | | 7/1983 | Beall et al. |
| 4,672,040 A | | 6/1987 | Josephson |
| 4,695,392 A | | 9/1987 | Whitehead et al. |
| 4,699,717 A | | 10/1987 | Riesner et al. |
| 4,767,670 A | | 8/1988 | Cox et al. |
| 4,861,705 A | | 8/1989 | Margel |
| 4,925,818 A | | 5/1990 | Schneider et al. |
| 4,927,750 A | | 5/1990 | Dorn |
| 5,057,426 A | | 10/1991 | Henco et al. |
| 5,075,430 A | | 12/1991 | Little |
| 5,076,950 A | | 12/1991 | Ullman et al. |
| 5,126,239 A | | 6/1992 | Livak et al. |
| 5,155,018 A | | 10/1992 | Gillespie et al. |
| 5,234,809 A | | 8/1993 | Boom et al. |
| 5,316,680 A | | 5/1994 | Frechet et al. |
| 5,346,994 A | | 9/1994 | Chomczynski |
| 5,389,449 A | | 2/1995 | Afeyam et al. |
| 5,395,498 A | | 3/1995 | Gombinsky et al. |
| 5,523,231 A | | 6/1996 | Reeve |
| 5,582,988 A | | 12/1996 | Backus et al. |
| 5,610,274 A | | 3/1997 | Wong |
| 5,652,348 A | | 7/1997 | Burton et al. |
| 5,658,548 A | | 8/1997 | Padhye et al. |
| 5,660,984 A | | 8/1997 | Davis et al. |
| 5,681,946 A | | 10/1997 | Reeve |
| 5,683,875 A | | 11/1997 | Lichtenwalter |
| 5,693,785 A | | 12/1997 | Woodward et al. |
| 5,728,822 A | | 3/1998 | Macfarlane |
| 5,734,020 A | | 3/1998 | Wong |
| 5,747,663 A | | 5/1998 | Colpan et al. |
| 5,783,686 A | | 7/1998 | Gonzalez |
| 5,789,148 A | | 8/1998 | Van Vlasselaer et al. |
| 5,861,315 A | | 1/1999 | Nakahata |
| 5,898,071 A | | 4/1999 | Hawkins |
| 5,904,848 A | | 5/1999 | Wong et al. |
| 5,945,525 A | | 8/1999 | Uematsu et al. |
| 5,990,301 A | | 11/1999 | Colpan et al. |
| 6,027,945 A | * | 2/2000 | Smith et al. ................. 436/526 |
| 6,045,697 A | | 4/2000 | Girot et al. |
| 6,051,380 A | | 4/2000 | Sosnowski et al. |
| 6,117,398 A | | 9/2000 | Bienhaus et al. |
| 6,270,970 B1 | * | 8/2001 | Smith et al. .................... 435/6 |
| 6,310,199 B1 | * | 10/2001 | Smith et al. ................ 536/25.4 |
| 6,344,326 B1 | | 2/2002 | Nelson et al. |

OTHER PUBLICATIONS

Bishoff et al, "Chemically Synthesized Hydrophobic Anion–Exchange High–Performance Liquid Chromatography Supports Used for Oligonucleotide Resolution By Mixed Mode Chromatography", *J. Chromatog.* (1983) 270:117–126.

Bishoff et al , "Nucleic Acid Resolution By Mixed–Mode Chromatography", *J. Chromatog.* (1984) 296:329–337.

Boom et al., "Rapid and Simple Method for Purification of Nucleic Acids", *J. Clin. Microbiol.,* (1990) 28:495–503.

Crowother et al . "High–Performance Liquid Chromatographic Separation of Oligonucleotides and Other Nucleic Acid Constituents on Multifunctional Stationary Phases", *J. Chromatog.* (1983) 282:619–628.

Edwardson et al., "Separation and purification of oligonucleotides using a new bonded–phase packing material", *J. Chromatog.* (1991) 545:79–89.

Figueroa et al, "High–Performance Immobilized–Metal Affinity Chromatography of Proteins on Iminodiacetic Acid Silica–Based Bonded Phases", *J. Chromatog.* (1986) 371:335–352.

Floyd et al., "Mixed–Mode Hydrophobic Ion Exchange for the Separation of Oligonucleotides and DNA Fragments Using HPLC", *Analytical Biochemistry* (1986) 154:570–577.

Gjerd et al., Ion Chromatography, Ch. 3, Dr. Alfred Hothig Verlag Heidelberg (1987) 2nd Ed.

Goldsborough et al., "High Purity Plasmid DNA from Anion Exchange Chromatography", *Focus* (1998) vol. 20, No. 3.

Jost et al., "Application of a Weakly Basic Dimethylamino–Modified Silica Ion Exchanger to the Separation of oligonucleotides", *J. Chromatog.* 185 (1979) 403–412.

Kirk–Othmer, Encyclopedia of Chemical Technology, (1993) Vol 6, 4th ed., pp. 773–775.

Kurt–Othmer Encyclopedia of Chemical Technology, vol. 21, 4th ed., Mary Howe–Grant, ed., John Wiley & Sons, pub., 1997, pp. 1021–1022.

Maa et al., "Rapid high–performance liquid chromatography of nucleic acids with polystyrene–based micropellicular anion exchangers", *J. Chromatog.* (1990) 508:61–73.

Macherey–Nagel, Macherey–Nagel homepage on the Internet on Jun. 12, 1998, at http://www.machrey–nagel.com.

Marko et al., "A Procedure for the Large–Scale Isolation of Highly Purified Plasmid DNA Using Alkaline Extraction and Binding to Glass Powder", *Anal. Biochem.* (1982)121:382–387.

McLaughlin, I., "Mixed–Mode Chromatography of Nucleic Acids", *Chem Rev* (1989) 89:309–319.

Northrop, et al., "Preparation and Evaluation of a Bimodal Size–Exclusion Chromatography Column Containing a Mixture of Two Silicas of Different Pore Diameter", *Anal. Chem.* (1991) 63:1350–1354.

Technical Bulletin No. 202 "Wizard ® Plus Series 9600 ™ DNA Purification System", (Promega Corp.) (1998).

Technical Bulletin No. 225 "Wizard ® Plus SV Minipreps DNA Purification System", (Promega Corp.) (1999).

Technical Bulletin No. 259 "Wizard ® PureFection Plasmid DNA Purification System", (Promega Corp.) (1999).

QuantiBlot, QuantiBlot Human DNA Quantitation System, PE Applied Biosystems, Feb. 5, 1996, pp. 1–5 (http://www.pebio.com/fo/773503.html).

Sambrook, J., et al. (1989) In *Molecular Cloning A Laboratory Manual,* 2nd edition, Cold Spring Harbor Laboratory Press, pp. 2.22 and filtration system reference.

Sambrook, J., et al., (1989) In *Molecular Cloning A Laboratory Manual,* 2nd edition, Cold Spring Harbor Laboratory Press, pp. 1.25–1.28.

Promega Corp., "Material Safety Data Sheet: Wizard® SV96 Neutralisation Solution" Jul. 2000 * Box 2 (composition/data on components): guanidinium chloride *.

Levison, et al., *Journal of Chromatography,* Dec. 1998, 827(2):337–344.

Uematsu et al., Database CAS online AN 126:182277 9 pp. Abstract (EP 0 757 106 A2).

Vogelstein, et al., *Proc. Natl. Acad. Sci* (1979) vol. 76, No. 2:615–619.

Waterborg et al., *Nucleic Acids Research* (1993) vol. 21, No. 12:2913–2915.

* cited by examiner

LYSATE CLEARANCE AND NUCLEIC ACID ISOLATION USING SILANIZED SILICA MATRICES

CROSS-REFERENCE TO RELATED APPLICATIONS

This is application is a continuation-in-part of U.S. application Ser. No. 09/475,958 filed Dec. 30, 1999, which claims the benefit of U.S. Provisional Application No. 60/134,156 filed May 14, 1999.

STATEMENT REGARDING FEDERALLY SPONSORED RESEARCH OR DEVELOPMENT

Not applicable.

TECHNICAL FIELD

This invention relates generally to methods of using modified silica matrices to clear solutions of disrupted biological material, such as cell lysates or homogenates of plant or animal tissue. This invention also relates to the use of such matrices to isolate target nucleic acids, such as plasmid DNA, chromosomal DNA, DNA fragments, total RNA, mRNA, or RNA/DNA hybrids from non-target material, such as proteins, lipids, cellular debris, and non-target nucleic acids. This invention relates, particularly, to the use of silanized silica matrices in lysate clearance and in target nucleic acid isolation.

BACKGROUND OF THE INVENTION

Various methods have been developed for isolating target nucleic acids from biological material or from other types of material containing the nucleic acids. When the target nucleic acid is contained in the interior of a cell, the cell membrane must be disrupted and the contents of the cell released into the solution surrounding the cell before the target nucleic acid can be isolated from other cellular material. Such disruption can be accomplished by mechanical means (e.g., by sonication or by blending in a mixer), by enzymatic digestion (e.g., by digestion with proteases), or by chemical means (e.g., by alkaline lysis followed by addition of a neutralization solution). Whatever means is used to disrupt a cell, the end product, referred to herein as a lysate solution, consists or the target material and many contaminants, including cell debris.

Centrifugation or filtration are commonly used to clear a lysate solution of as many of the large contaminants as possible before the target nucleic acid material is isolated therefrom. Unfortunately, neither filtration nor centrifugation is readily amenable to automation. Specifically, neither are typically performed at basic pipettor-diluter robotics stations, such as the Biomek®-2000 (Beckman Coulter, Inc.; Fullerton, Calif.).

Many materials and methods have been developed for use in the isolation of nucleic acids from cleared lysate solutions. One such method is extraction of a nucleic acid from an agarose gel after fractionation of the nucleic acid by gel electrophoresis. Known means of extraction of nucleic acids from gel slices include dialysis, solvent extraction, and enzymatic digestion of the agarose. Such systems of nucleic acid extraction from an agarose gel slice tend to be very labor-intensive, and not amenable to automation. Furthermore, smaller sized fragments of DNA or RNA (i.e., below about 100 base pairs) tend to be lost in the extraction process.

Other systems of nucleic acid extraction are silica based, such as those which employ controlled pore glass, filters embedded with silica particles, silica gel particles, resins comprising silica in the form of diatomaceous earth, glass fibers or mixtures of the above. Each such silica-based solid phase separation system is configured to reversibly bind nucleic acid materials when placed in contact with a medium containing such materials in the presence of chaotropic agents. The silica-based solid phases are designed to remain bound to the nucleic acid material while the solid phase is exposed to an external force such as centrifugation or vacuum filtration to separate the matrix and nucleic acid material bound thereto from the remaining media components. The nucleic acid material is then eluted from the solid phase by exposing the solid phase to an elution solution, such as water or an elution buffer. Numerous commercial sources offer silica-based resins designed for use in centrifugation and/or filtration isolation systems, e.g., Wizard® DNA purification systems products from Promega Corporation (Madison, Wis., U.S.A.), or the QiaPrep® DNA isolation systems from Qiagen Corp. (Chatsworth, Calif., U.S.A.). Unfortunately, the type of silica-based solid phases described above all require one to use centrifugation or filtration to perform the various isolation steps in each method, limiting the utility of such solid phases in automated systems.

Magnetically responsive solid phases, such as paramagnetic or superparamagnetic particles, offer an advantage not offered by any of the silica-based solid phases described above. Such particles could he separated from a solution by turning on and off a magnetic force field, by moving a container on to and off of a magnetic separator, or by moving a magnetic separator on to and off of a container. Such activities would be readily adaptable to automation.

Magnetically responsive particles have been developed for use in the isolation of nucleic acids by the direct reversible adsorption of nucleic acids to the particles. See, e.g., silica gel-based porous particles designed to reversibly bind directly to DNA, such as MagneSil™ Paramagnetic Particles (Promega), or BioMag® Paramagnetic Beads (Polysciences, Warrington, Pa., U.S.A.). See also U.S. Pat. No. 6,027,945. Magnetically responsive glass beads of a controlled pore size have also been developed for the isolation of nucleic acids. See, e.g. Magnetic Porous Glass (MPG) particles from CPG, Inc. (Lincoln Park, N.J. U.S.A.), or porous magnetic glass particles described in U.S. Pat. Nos. 4,395,271; 4,233,169, or 4,297,337. Nucleic acid material tends to bind very tightly to glass, however, so that it can be difficult to remove nucleic acids from such magnetic glass particles, once bound thereto. As a result, elution efficiencies from magnetic glass particles tend to be low compared to elution efficiencies from particles containing lower amounts of a nucleic acid binding material such as silica.

A variety of silica matrices have also been developed which consist of a silica solid phase with ligands covalently attached thereto designed to participate in ion exchange or in reversed-phase interaction with nucleic acids. However, such systems are generally designed for use as a solid phase of a liquid chromatography system, for use in a filtration system, or for use with centrifugation to separate the solid phase from various solutions. Such systems range in complexity from a single species of ligand covalently attached to the surface of a filter, as in DEAE modified filters (e.g., CONCERT® isolation system. Life Technology Inc., Gaithersburg, Md., U.S.A.), to a column containing two different solid phases separated by a porous divider (e.g., U.S. Pat. No. 5,660,984), to a chromatography resin with pH dependent ionizable ligands covalently attached thereto (e.g., U.S. Pat. No. 5,652,348), to mixed-mode or mixed-bed resins with ion exchange ligands and reversed-phase ligands on the same or on different solid phase components of the resins, respectively (e.g., McLaughlin, L. M., *Chem Rev* (1989) 89:309–319).

Matrices have also been developed which are designed to reversibly bind to specific target materials through affinity interaction. Some such matrices use affinity of the poly (A) tail of mRNA for oligo (dT) to isolate mRNA, either by attaching oligo (dT) directly to the surface of a solid phase (e.g., U.S. Pat. No. 5,610,274), or by providing a solid phase coated with streptavidin and biotinylated oligo (dT) which naturally binds to both the streptavidin and to mRNA in a solution (e.g., PolyATract® Series 9600™ mRNA Isolation System from Promega Corporation (Madison, Wis., U.S.A.); and ProActive® streptavidin coated microsphere particles from Bangs Laboratories (Carmel, Ind., U.S.A.)).

Silanization has been used as a coupling agent to facilitate the covalent attachment of various ligands to the silica solid phases to produce chromatographic matrices for the isolation of solutes, such as nucleic acids. See, e.g., U.S. Pat. No. 4,672,040 (col. 13, lines 3–22); U.S. Pat. Nos. 5,734,020; 4,695,392; and 5,610,274). In such reactions a silane compound, such as 3-glycidoxypropyltrimethoxysilane, is reacted with the surface of a solid phase, such as a silica based material or with an iron oxide, such that the silane becomes attached thereto. The resulting matrix includes highly reactive residues, such as the epoxide group at the terminus of the alkoxy chain of 3-glycidoxypropyltrimethoxysilane, which remain available after reaction with the surface of the solid phase. Matrices with such reactive groups have been used as intermediaries in the production of ion exchange, reversed-phase, mixed-bed, mixed-mode, and affinity resins.

Each of the systems described above has its limitations in terms of solution conditions required for the isolation of nucleic acids, and in terms of the class of substrates from which it can best isolate nucleic acids. To date, no materials and methods have been developed which can be used to isolate low molecular weight nucleic acids, (e.g., under 100 base pairs) as efficiently as higher molecular weight nucleic acids from substrates such as vegetable oils or agarose gel slices. With the modern need to detect viruses and evidence of genetic modification of vegetable matter from which such oils are produced, there is a great need to be able to isolate small quantities of nucleic acids from such substrates. Materials and methods are also needed which enable one to automate as many steps as possible to quickly and efficiently isolate target nucleic acids from cells or mammalian tissue. Specifically, methods and materials are needed for the clearing of solutions of disrupted biological material, and for the isolation of target nucleic acids from such cleared solutions, wherein labor-intensive steps such as filtration or centrifugation are not required. The present invention addresses each of these needs.

BRIEF SUMMARY OF THE INVENTION

The method of the present invention provides a means for clearing a solution of disrupted biological material, using a first silica solid phase with a plurality of first silane ligands covalently attached thereto, wherein the first silane ligands are designed to adsorb to non-target nucleic acid in the disrupted biological material. The method of the present invention also provides a means for isolating a target nucleic acid from a solution, such as a cleared lysate solution, comprising the target nucleic acid and at least one non-target material using a second silica solid phase with a plurality of second silane ligands covalently attached thereto, wherein the second silane ligands are designed to adsorb selectively to the target nucleic acid in a nucleic acid adsorption solution. In a preferred embodiment of the method of the present invention, a solution of disrupted biological material is cleared with the first silica solid phase in the first solution, and target nucleic acid material removed from the resulting cleared lysate by adsorption to the second silica solid phase in a nucleic acid adsorption solution.

In the first embodiment of the present method described above, a solution of disrupted biological material, such as a cell lysate or a homogenate of mammalian tissue, is cleared according to steps comprising: (a) providing a first silanized silica matrix, comprising a silica solid phase with a plurality of silane ligands covalently attached thereto, and (b) combining the first silanized silica matrix with a first solution, comprising a disrupted biological material, a target nucleic acid, and a chaotropic salt concentration sufficiently high to promote selective adsorption of the disrupted biological material to the matrix, thereby forming a first complex. The disrupted biological material is preferably introduced to the matrix in the presence of a chaotropic salt concentration sufficiently high to promote selective adsorption of the disrupted non-target biological material to the matrix, leaving the target nucleic acid in solution.

In the second embodiment or the method of the present invention described above, a target nucleic acid is isolated from a second solution, a nucleic acid adsorption solution comprising the target nucleic acid and at least one non-target material. The second solution can be from any one of a number of different sources including, but not limited to, a cleared lysate, a vegetable oil, a cleared homogenate of mammalian tissue, a cleared lysate of vegetable material, or a solution comprising a target nucleic acid fractionated by gel electrophoresis in an agarose gel. This embodiment of the method comprises the steps of: (a) providing a second silanized silica matrix comprising a silica solid phase with a plurality of silane ligands of general formula (I), below, covalently attached thereto; (b) combining the second silanized silica matrix with the nucleic acid adsorption solution, wherein the pH of the nucleic acid adsorption solution is less than about pH 8.0 and the concentration of chaotropic salt in the solution is sufficiently low that the target nucleic acid is selectively adsorbed to the second silanized silica matrix, thereby forming a second complex.

Each of the plurality of silane ligands of the first and second silanized silica matrix is preferably of the general formula (I):

wherein $R_1$ and $R_2$ are each a subunit selected from the group consisting of a hydrocarbon chain having from 1 to 5 carbon atoms, an alkoxy having from 1 to 5 carbon atoms, a hydroxyl, an alkyl chain having from 4 to 10 carbon atoms interrupted by an oxy residue wherein up to five of the carbon atoms is substituted by a group selected from the group consisting of a halogen, an alkoxy having from 1 to 3 carbon atoms, a cyano having from 1 to 3 carbon atoms, and a hydroxy; wherein $R_3$ is a hydrocarbon chain having from 1 to 20 carbon atoms substituted by at least one hydroxy, an alkyl chain having from 4 to 20 carbon atoms interrupted by at least one oxy group wherein up to ten carbon atoms are replaced by a moiety selected from the group consisting of a halogen, a cyano having from 1 to 3 carbon atoms, an alkoxy having from 1 to 3 carbon atoms, a hydroxy, and an epoxy. $R_1$ and $R_2$ may also independently be linkages to other silane ligands to generate higher order polymers.

In yet another embodiment, the present invention consists of a kit comprising, in a single container, a plurality of silanized silica magnetic particles comprising a silica solid phase with a plurality of silane ligands covalently attached to the surface of each particle, each ligand having a structure of formula (I), above.

The methods and materials of the present invention can be used to isolate target nucleic acids including, but not limited to, plasmid DNA, DNA fragments, total RNA, mRNA, RNA/DNA hybrids, amplified nucleic acids, and genomic DNA from a variety of contaminants, including but not limited to agarose from an agarose gel, non-target nucleic acids, and non-target components of bacteria, animal tissue, blood cells, and vegetable oil or other plant material. The methods and materials of the present invention are efficient at isolating both low molecular weight DNA molecules (i.e., less than about 150 base pairs) and larger molecular weight DNA. Applications of the methods and compositions of the present invention to isolate nucleic acids from a variety of different media will become apparent from the detailed description of the invention below. Those skilled in the art of this invention will appreciate that the detailed description of the invention is meant to be exemplary only and should not be viewed as limiting the scope of the invention.

DETAILED DESCRIPTION OF THE INVENTION

A. Definitions

Figure 1:
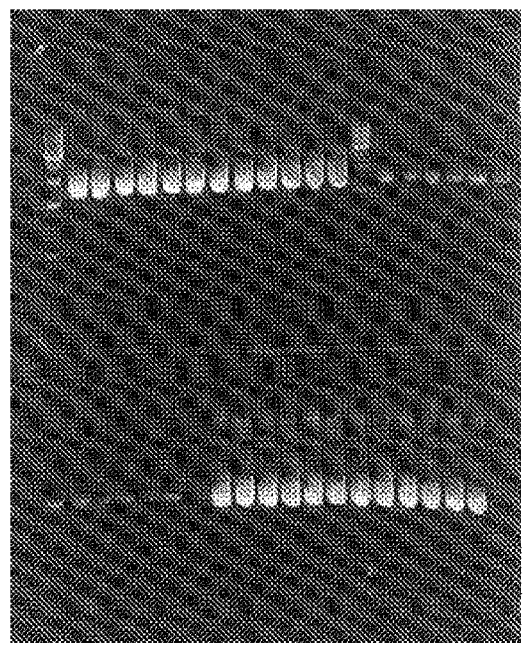
FIG. 1 is a photograph of plasmid DNA isolated from a lysate of *E. coli* bacteria cells using various means described in Example 5, below, after fractionation on an agarose gel by gel electrophoresis.

The term "alkyl chain" as used herein refers to a straight chain alkane optionally substituted with at least one oxygen, nitrogen, or sulfur atom.

The term "chaotropic agent" as used herein refers to salts of particular ions which, when present in a sufficiently high concentration in an aqueous solution, cause proteins present therein to unfold and nucleic acids to lose secondary structure. It is thought that chaotropic ions have these effects because they disrupt hydrogen-bonding networks that exist in liquid water and thereby make denatured proteins and nucleic acids thermodynamically more stable than their correctly folded or structured counterparts. Chaotropic ions include guanidinium, iodide, perchlorate, and trichloroacetate. Chaotropic agents include guanidine hydrochloride, guanidine thiocyanate (which is sometimes referred to as guanidine isothiocyanate), sodium iodide, sodium perchlorate, and sodium trichloroacetate.

The term "disrupted biological material" as used herein refers to material, other than target nucleic acid, released when biological materials, such as bacteria cells, mammalian tissue, blood cells, or plant material are disrupted. Disrupted biological material includes, but is not limited to proteins, lipids, cellular debris, and non-target nucleic acids.

The term "glass particles" as used herein means particles of crystalline or vitreous silicas, even though crystalline silicas are not formally "glasses" because they are not amorphous, or particles of glass made primarily of silica. The term includes quartz, vitreous silica, controlled pore glass particles, and glass fibers.

The term "magnetic" as used to refer to silica magnetic particles includes materials which are paramagnetic or superparamagnetic materials. The term "magnetic", as used herein, also encompasses temporarily magnetic materials, such as ferromagnetic or ferrimagnetic materials. Except where indicated otherwise below, the silica magnetic particles used in this invention preferably comprise a superparamagnetic core coated with siliceous oxide, having a hydrous siliceous oxide adsorptive surface (i.e. a surface characterized by the presence of silanol groups).

The term "nucleic acid" as used herein refers to any DNA or RNA molecule or a DNA/RNA hybrid molecule. The term includes plasmid DNA, amplified DNA or RNA fragments, total RNA, mRNA, genomic DNA, and chromosomal DNA.

The term "pH dependent ion exchange silica magnetic particles", as used herein, refers to silica magnetic particles with a plurality of ion exchange ligands covalently attached thereto, which can act as cation exchangers at one pH and as anion exchangers at another pH. Such magnetic particles are particularly well suited for use in the methods and kits of the present invention, because substrates can selectively adsorb to the hydrous siliceous oxide adsorptive surface of the particle through hydrophobic interactions, to the ion exchange ligands through ion exchange, or to both the surface and ion exchange ligands, depending upon solution conditions.

The term "solid phase" is used herein in a standard chromatographic sense, to refer to an insoluble, usually rigid, matrix or stationary phase which interacts with a solute, in this case a target nucleic acid, in a solute mixture. The term solid phase, as used herein, specifically includes stationary phases in liquid chromatography (LC), high pressure liquid chromatography (HPLC), particulate matrices embedded into or bound to filters, and magnetic or non-magnetic porous matrix particles which interact with solutes when added directly to a solute mixture.

The term "silica gel" as used herein refers to chromatography grade silica gel, a substance which is commercially available from a number of different sources. Silica gel is most commonly prepared by acidifying a solution containing silicate, e.g. by acidifying sodium silicate to a pH of less than 11, and then allowing the acidified solution to gel. See, e.g. silica preparation discussion in *Kurt-Othmer Encyclopedia of Chemical Technology*, Vol. 21, 4th ed., Mary Howe-Grant, ed., John Wiley & Sons, pub., 1997, p. 1021.

As used herein, the term "silica magnetic particles" refers to silica based solid phases which are further comprised of materials which have no magnetic field but which form a magnetic dipole when exposed to a magnetic field, i.e., materials capable of being magnetized in the presence of a magnetic field but which are not themselves magnetic in the absence of such a field.

The term "surface", as used herein, refers to the portion of the support material of a solid phase which comes into direct contact with a solution when the solid phase is combined therewith.

The term "target nucleic acid" as used herein refers to the particular species of nucleic acid to be isolated in any particular application of the methods of the present invention. The target nucleic acid is preferably DNA, preferably DNA of less than about 60 kilobase pairs, preferably at least about 1000 base pairs, more preferably at least about 500 base pairs, more preferably at least about 250 base pairs, more preferably still at least about 150 base pairs, more preferably at least about 100 base pairs, and even more preferably at least about 50 base pairs. The target nucleic acid is preferably DNA of at least 25 base pairs.

The methods and kits of the present invention can be used to clear a solution of disrupted biological material, and/or to isolate a target nucleic acid from a solution, preferably from a solution of cleared disrupted biological material. In at least one step of the method, a complex is formed in a solution between a matrix and a solid phase, preferably a magnetic particle matrix. The resulting complex is then isolated from or removed from the solution. When the matrix is a magnetic particle, it is preferably removed in the presence of a magnetic field. Magnetic particles or other solid phases suitable for use in any given step of the methods and kits of the present invention have the capacity to form a complex with the solute of interest in that particular step of the method.

The solute is the type of material to be isolated from or removed from a solution, using a matrix, according to a method of the present invention. Disrupted biological material is the solute in the lysate or homogenate clearing method of the invention. A target nucleic acid is the solute when a matrix is used to isolate the target nucleic acid from any solution comprising the target nucleic acid and other material, such as a cleared lysate, a vegetable oil, or a cleared homogenate of mammalian tissue.

Conditions which promote the formation of a matrix/solute complex vary, depending upon the nature of the solute and on the characteristics of the matrix. For example, when the matrix is ion exchange magnetic particles or pH dependent ion exchange particles, the complex is preferably formed as a result of ion exchange between the solute and ion exchange ligands at the surface of the particles. In order to promote such ion exchange interaction, there must be at least some salt present in the solution to promote ion exchange with the solute, and the pH of the solution must be within the range wherein the ion exchange ligand has a charge appropriate to exchange with the solute. When the matrix is silica or silica magnetic particles, the complex is preferably formed as a result of hydrophobic interactions between the solute and particles. When the matrix is pH dependent ion exchange silica magnetic particles, the complex can be formed as a result of hydrophobic interactions between the solute and the siliceous oxide surface of the particles, as a result of ion exchange between the solute and the ion exchange ligands, or as a result of a combination of the two types of interactions. When the matrix is silanized silica or silanized silica magnetic particles, the complex is preferably formed under conditions which promote hydrogen bonding between the solute and the matrix.

When the solute is a disrupted biological material, such as one finds in a cell lysate or tissue homogenate, and the matrix is silica magnetic particles or pH dependent ion exchange silica magnetic particles, the matrix/solute complex is preferably formed in a solution which does not contain any more than trace amounts of alcohol or of chaotropic salts. Both alcohol and chaotropic salts, such as guanidine thiocyanate or guanidine isothiocyanate, promote adsorption of nucleic acid materials to such particles. It is contemplated, however, that one could practice the present method of cell lysate clearance in the presence of alcohol or chaotropic salts if the concentration of such silica magnetic or pH dependent ion exchange particles in a homogenate or lysate solution were low enough to clear the solution, but not high enough to adhere to a significant amount of the target nucleic acid in the solution.

When the solute is a disrupted biological material and the matrix is a first silanized silica solid phase, such as first silanized silica magnetic particles, the matrix/solute complex, a first complex, is preferably formed in a first solution comprising a sufficiently high concentration of a chaotropic salt to promote the selective adsorption of disrupted biological material to the matrix. The concentration of chaotropic salt required to promote adsorption to the matrix will depend upon the composition of and concentration of silane ligands attached to the surface of the solid phase of the silanized silica matrix, and upon the nature of the disrupted biological material to be adsorbed thereto. A concentration of any chaotropic salt sufficient to promote selective adsorption of any given disrupted biological material to any given silanized silica matrix can be determined through a simple titration experimentation. When a chaotropic salt is present, the chaotropic salt concentration is preferably no more than 3.5M, more preferably no more than about 3.0M. When other salts, such as potassium acetate or sodium chloride, are present in the first solution, the concentration of chaotropic salt required to promote adsorption of the disrupted biological material to the matrix may vary.

When the solute is a target nucleic acid, formation of the complex is preferably done in the presence of at least one agent known to promote reversible adsorption of the target nucleic acid to the magnetic particles. The reversible adsorption reaction is preferably done through specific adsorption between the target nucleic acid and magnetic particles, leaving non-target material in solution. For example, when the target nucleic acid is plasmid DNA being isolated from a cleared lysate solution, the plasmid DNA is combined with a matrix under conditions wherein the plasmid DNA forms a complex therewith while non-target materials, such as proteins, lipids, and chromosomal DNA remain in solution. When the matrix is an ion exchange matrix, the complex is formed in the presence of a counterion and in a solution with a pH at which the ion exchange ligands have the capacity to exchange with the target nucleic acid. When the matrix is silica or silica magnetic particles, formation of the complex is preferably done in the presence of an agent selected from the group consisting of a low molecular weight alcohol, a high concentration of a non-chaotropic salt, and a chaotropic salt, or a combination of any of the above. For methods of adsorption and desorption of target nucleic acids to such silica magnetic particles, which are suitable for use in the present invention, see international patent application number PCT/US98/01149 for METHODS OF ISOLATING BIOLOGICAL TARGET MATERIALS USING SILICA MAGNETIC PARTICLES, published as WO 98/31840, incorporated by reference herein.

When the matrix is a second silanized silica matrix, such as second silanized silica magnetic particles, the matrix/nucleic acid eluent complex is formed in a nucleic acid adsorption solution configured to promote adsorption of nucleic acids to the matrix through hydrogen bond formation. Preferred conditions for the promotion of hydrogen bond formation with the second silanized matrix are discussed herein below.

In one aspect, the present invention is a method of using a first silanized silica matrix to clear a first solution, comprising disrupted biological material, a target nucleic acid, and a chaotropic salt, of the disrupted biological material. Once a first complex is formed, the first solution can be cleared by separating the first complex from the solution.

Any one of a number of different means can be used to separate the first complex from the solution, depending upon the nature of the silanized silica matrix. When the solid phase of the silanized silica matrix is a silica magnetic particle (hereinafter, a "silanized silica magnetic particle"), the matrix can be separated from the first complex by centrifugation, by filtration, or using a magnetic field. The matrix is preferably silanized silica magnetic particles, and the first complex is preferably separated from the first solution in the presence of a magnetic field. Use of a magnetic field and magnetic particles is preferred, because they enable one to automate the isolation process. When the solid phase of the silanized silica matrix is glass fiber or diatomaceous earth or other similarly solid forms of silica material, the complex is preferably separated from the first solution using centrifugation or filtration.

The cleared solution produced as described above will contain at least some non-target material, such as disrupted biological material which did not adsorb to the first silanized silica matrix in the first solution. Various methods can suitably be used to isolate the target nucleic acid from the cleared solution, including but not limited to adsorption of the target nucleic acid to a second silanized silica matrix in a nucleic acid adsorption solution, as described herein below, alcohol precipitation of the nucleic acid, and adsorption of the target nucleic acid to silica magnetic particles (e.g. MagneSil™ Paramagnetic Particles (Promega) or Controlled Pore Glass Particles (CPG, Inc., New Jersey)), use of a solution-based nucleic acid isolation procedure (e.g., *Molecular Cloning* $2^{nd}$ ed, edited by Sambrook, et al., 1.21–1.52 (1989)), agarose gel purification, capillary gel electrophoresis, or use of one of many other solid phase based procedures (e.g., Wizard® Plus SV Minipreps (Promega)), all of which are incorporated by reference herein. pH dependent ion exchange silica magnetic particles can also be used. (Bitner et al., *Advances in Nucleic Acid and Protein Analyses, Manipulation, and Sequencing* Proceedings of SPIE Vol. 3926 (2000) pp. 126–133 and U.S. patent application Ser. No. 09/312,172 filed May 14, 1999, both of which are incorporated by reference herein). When the target nucleic acid is mRNA, it is preferably isolated from the cleared solution using a system which utilizes oligo(dT) to specifically adsorb to the poly(A) tail of mRNA (e.g. PolyATract mRNA Isolation System (Promega); U.S. Pat. Nos. 5,734,020 or 5,610,274). Where the target nucleic acid contains a specific, unique sequence not shared by non-target nucleic acids, it can also be isolated using an oligonucleotide complementary to the sequence immobilized on a support surface (e.g. U.S. Pat. No. 5,683,875).

This particular embodiment of the present method provides an excellent means for efficient clearing of a solution of disrupted biological material, thereby increasing the efficiency of techniques used to further isolate the target nucleic acid from the resulting cleared solution. The same type of matrix used to clear the disrupted biological material, i.e. a silanized silica matrix, can also be used to isolate the target nucleic acid from the cleared solution, or from other solutions, as described below.

In another embodiment of the present method, a second silanized silica matrix is combined with a nucleic acid adsorption solution comprising the target nucleic acid and at least one non-target material under conditions designed to promote adsorption of the target nucleic acid to the second silanized matrix through hydrogen bond formation. The nucleic acid adsorption solution can be, for example, a cleared bacterial lysate solution, a cleared homogenate of mammalian tissue, a cleared lysate of plant tissue, vegetable oil, or a solution of a nucleic acid from an agarose gel slice and the agarose gel. The nucleic acid adsorption solution preferably has a pH of up to pH 8.0, preferably at a pH of less than about 7.0, and more preferably in a solution of pH of less than about 6.0. The pH of the nucleic acid adsorption solution is preferably at least about pH 3.5, more preferably at least about pH 4.0. If the nucleic acid solution includes chaotropic salt, the chaotropic salt concentration is sufficiently low to allow selective adsorption of the target nucleic acid to the matrix, leaving the non-target material in solution. When the chaotropic salt is guanidine thiocyanate, it is preferably present in the first solution at a concentration of about 0.2 to about 1.0 M, more preferably about 0.3 to about 0.5 M, most preferably about 0.4 M guanidine thiocyanate. When the chaotropic salt is guanidine hydrochloride, it is preferably present in the first solution at a concentration of about 0.4 to about 1.2 M, more preferably about 0.5 to about 0.7 M, most preferably about 0.6 M guanidine hydrochloride. When other salts, such as potassium acetate or sodium chloride, that are not chaotropic agents are present in the first solution, the concentration of chaotropic salt in the nucleic acid adsorption solution which will allow adsorption of the nucleic acid to the second matrix may vary.

The nucleic acid adsorption solution preferably further comprises a low molecular weight alcohol, such as ethanol or isopropanol. When the alcohol is isopropanol, it is preferably present at a concentration of at least 25% and up to about 50%, more preferably at least 30% and up to about 45% by volume. When the alcohol is ethanol, it is preferably present at a concentration of at least 50% and up to about 90%, more preferably at least 60% and up to about 80% by volume.

Once the second complex is formed, it is can be separated from the solution using any of the separation means described as suitable for use in separating the first complex from the first solution, above.

The second complex is preferably washed at least once with a wash solution to remove salts or other contaminants non-specifically associated with the complex. The wash solution preferably has a pH of no more than about pH 8.0, more preferably a pH of no more than about pH 6.0. The wash solution preferably comprises water, more preferably "Nanopure®" water (Millipore, Bedford, Mass., U.S.A.) distilled deionized water, or Nuclease-Free Water (Promega). When the density of silane ligands on the surface of the second silanized magnetic particle is sufficiently low, the target nucleic acid will be released from the second complex in a water wash. In such circumstances, the wash solution preferably further comprises a low molecular weight alcohol, such as ethanol or isopropanol. The target nucleic acid will remain adsorbed to the second silanized silica matrix in the presence of wash solutions of varying non-chaotropic salt concentrations (e.g., 300 mM to about 5M NaCl), provided the pH of the solution remains sufficiently low. At least one of the wash solutions used in the wash step preferably has a salt concentration of at least 1M. The second complex is most preferably washed at least three times prior to elution, as described below.

The target nucleic acid can be eluted from the second complex without any wash steps. However, the wash steps ensure a more complete isolation of the target-nucleic acid from non-target materials, and are therefore preferred. The target nucleic acid is preferably eluted from the second complex by combining the complex with an elution solution with a pH of at least about pH 8.0, more preferably at least about pH 9.0, and most preferably at least about pH 9.5.

When the target nucleic acid is plasmid DNA, the silanized silica matrix of the present invention can be added directly to a cleared lysate of bacteria transformed with the plasmid DNA, lysed with an alkaline lysis solution, and treated with a "neutralization solution", provided that solution conditions are adjusted as needed to promote adsorption of the plasmid DNA to the matrix. Alkaline lysis procedures suitable for use in the present invention can be found in Sambrook et al, *Molecular Cloning*, Vol. 1, $2^{nd\ ed.}$ (pub. 1989 by Cold Spring Harbor Laboratory Press), pp. 1.25–1.28, and in Technical Bulletin No's 202, 225, and 259 (Promega Corp.). The neutralization solutions used in such procedures, in fact, lower the pH of the lysate solution to below pH 5.0, a pH at which plasmid DNA will readily adsorb to the silanized silica matrix, provided that the concentration of any chaotropic salt in the solution is sufficiently low to allow selective adsorption of DNA to the matrix. A low molecular weight alcohol is preferably added to the cleared lysate to dilute any chaotropic salt and promote such adsorption. Once adsorbed to the matrix to form the second complex, the complex can be washed and treated as described above to elute the plasmid DNA therefrom.

When the target nucleic acid is RNA or a type of DNA other than plasmid DNA, adsorption of the target nucleic acid to the matrix is preferably carried out under conditions designed to promote preferential adsorption of the target to the matrix. When both RNA and DNA are present in a solution, the non-target nucleic acid material can be digested using RNase or DNase, respectively, to eliminate the non-target material prior to adsorption of the target material to the matrix. In some circumstances, the solution conditions can also be designed to promote preferential adsorption of the specific target nucleic acid to the matrix. The specific solution conditions required to preferentially promote adsorption and desorption of DNA or RNA to the matrix will depend upon the characteristics of the matrix itself, and must therefore be determined for each embodiment of the matrix used in a given application.

The silanized silica matrix used in the method and included in the kit of the present invention comprises a silica solid phase, with a plurality of silane ligands covalently attached thereto. The silica solid phase of the silanized silica matrix comprises silica, preferably in the form of silica gel, siliceous oxide, solid silica such as glass fiber, glass beads, or diatomaceous earth, or a mixture of two or more of the above. Compositions of the silica solid phase suitable for use in the matrices of the present invention include the mixture of silica gel and glass described in U.S. Pat No. 5,658,548, the silica magnetic particles described in PCT Publication Number WO 98/31840, and solid phases sold by Promega Corporation for use in plasmid DNA isolation, i.e. Wizard® Minipreps DNA Purification Resin. Silica gel particles are particularly preferred for use as the silica solid phase in the silica matrices used in the present invention. Silica gel particles are stable at much higher pressures than solid phases made from soft gel support material, making the silica gel solid phases suitable for HPLC as well as LC and batch separation applications.

The matrix used in the method and kit of the present invention is preferably in a form which can be separated from a solute mixture comprising the target nucleic acid and at least one contaminant after the solute mixture is combined therewith, by application of an external force. A skilled artisan would appreciate that the type of external force suitable for use in separating the matrix from the solute mix depends upon the form in which the matrix is presented to the solute mix, and upon the physical properties of the solid phase component of the matrix. For example, gravity can be used to separate a silanized silica matrix from the solute mix when the matrix is in the form of a chromatographic resin loaded on an LC column, when the solid phase of the matrix is in the form of silica particles (e.g., controlled pore glass, silica gel particles, or silica magnetic particles) which are added batch-wise to a solute mixture and then separated therefrom by decantation or filtration, or when the matrix is in the form of a silica fiber or a filter with silica solid phase in the form of particles or chromatographic resin embedded into or attached thereto.

The external force used in the method of isolation is high pressure liquid when the matrix is the stationary phase of a high pressure liquid chromatography column (HPLC). Other forms of external force suitable for use in the method of this invention include vacuum filtration (e.g. when the solid phase component of the matrix is particles of controlled pore glass, particles of silica gel or silica magnetic particles, or mixtures of one or more of the above types of particles embedded into or attached to a filter), centrifugation (e.g. when the matrix is particulate, including magnetic particles), or magnetic (e.g. when the matrix comprises magnetic or paramagnetic particles).

When the solid phase component of the matrix is a silica gel particle, it is most preferably a silica magnetic particle. A silica magnetic particle can be separated from a solution using any of the external means described above for use with other types of solid phases, such as those described above. However, unlike the other solid phases, a silica magnetic particle can be separated from a solution by magnetic force, a quick and efficient means of separating a matrix from a solution.

When the solid support component of the matrix is a silica magnetic particle, the size of the particle is preferably selected as follows. Smaller silica magnetic particles provide a greater surface area (on a per weight unit basis) for modification as described herein below. However, smaller particles are limited in the amount of magnetic material which can be incorporated into such particles compared to larger particles. The median particle size of the silica magnetic particles used in a particularly preferred embodiment of the present invention is about 1 to 15 μm, more preferably about 3 to 10 μm, and most preferably about 4 to 7 μm. The particle size distribution may also be varied. However, a relatively narrow monodal particle size distribution is preferred. The monodal particle size distribution is preferably such that about 80% by weight of the particles are within a 10 μm range of the median particle size, more preferably within an 8 μm range, and most preferably within a 6 μm range.

The solid support component of the matrix of the present invention can be porous or non-porous. When the solid support is porous, the pores are preferably of a controlled size range sufficiently large to admit the target nucleic acid material into the interior of the solid phase particle, and to bind to functional groups or silica on the interior surface of the pores. However, the solid support is preferably porous to ensure sufficient ligand density to form a complex with either solute described above, i.e. the disrupted biological material or the target nucleic acid. The total pore volume of a silica magnetic particle, as measured by nitrogen BET method, is preferably at least about 0.2 $m^2/g$ of particle mass. The total pore volume of porous silica magnetic particles particularly preferred for use as components of the silanized silica matrix used in the present invention, as measured by nitrogen BET, is preferably at least about 50% of the pore volume, and is contained in pores having a diameter of 600 Å or greater.

Silica magnetic particle solid phases may contain substances, such as transition metals or volatile organics, which could adversely affect the utility of target nucleic acids substantially contaminated with such substances. Specifically, such contaminants could affect downstream processing, analysis, and/or use of the such materials, for example, by inhibiting enzyme activity or nicking or degrading the target nucleic acids isolated therewith. Any such substances present in the silica magnetic particle components of the matrices used in the present invention are preferably present in a form which does not readily leach out of the particle and into the isolated biological target material produced according to the methods of the present invention. Iron is one such undesirable at least one contaminant, particularly when the biological target material is a target nucleic acid.

Iron, in the form of magnetite, is present at the core of particularly preferred forms of silica magnetic particles used as the solid phase component of the matrices of the present invention. Iron has a broad absorption peak between 260 and 270 nanometers ("nm"). Target nucleic acids have a peak absorption at about 260 nm, so iron contamination in a target nucleic acid sample can adversely affect the accuracy of the results of quantitative spectrophotometric analysis of such samples. Any iron containing silica magnetic particles used to isolate target nucleic acids using the present invention preferably do not produce isolated target nucleic acid material sufficiently contaminated with iron for the iron to interfere with spectmophotometric analysis of the material at or around 260 nm.

The most preferred silica magnetic particles used as solid phases in the silanated silica magnetic particles in the methods and kits of the present invention are siliceous oxide coated particles described in international patent application publication number WO 98/31461. The description of the silica magnetic particles contained in the international application is incorporated by reference herein. The preferred silica magnetic particles leach no more than 50 ppm, more preferably no more than 10 ppm, and most preferably no more than 5 ppm of transition metals when assayed as follows. Specifically, the particles are assayed as follows: 0.33 g of the particles (oven dried @ 110° C.) are combined with 20 ml. of 1N HCl aqueous solution (using deionized water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred. Silica magnetic particles which meet the above-cited specification for particularly preferred particles are sold under the brand name MagneSil™ Paramagnetic Particles (Promega Corporation).

Any source of magnetic force sufficiently strong to separate the silica magnetic particles from a solution would be suitable for use in the nucleic acid isolation methods of the present invention. However, the magnetic force is preferably provided in the form of a magnetic separation stand, such as one of the MagneSphere® Technology Magnetic Separation Stands (cat. no.'s Z5331 to 3, or Z5341 to 3) from Promega Corporation.

The silanized silica matrix used in the present invention is preferably made using a silanization reagent of the general formula $$R_0R_1R_2SiR_3 \qquad (II)$$

wherein $R_0$ corresponds to one alkoxy radical having from 1 to 10 carbon atoms, preferably —$OCH_3$, —$OC_2H_5$ or —$OC_3H_7$, or one halogen atom, preferably —Cl, or one dialkyl amino group with identical or different alkyl radicals having from 1 to 6 carbon atoms, $R_1$ and $R_2$ correspond to a hydrocarbon radical having from 1 to 10 carbon atoms, —$CH_3$, —$C_2H_5$ or $C_3H_7$, or an alkoxy radical having from 1 to 10 carbon atoms, preferably —$OCH_3$, —$OC_2H_5$, or —$C_3H_7$, or one halogen atom or one alkyl radical having from 4 to 20 carbon atoms interrupted by at least one oxy or amino group, wherein said radical can also be replaced once or more by halogen, cyano, nitro, amino, monoalkylamino, dialkylamino, hydroxy or aryl, and $R_3$ corresponds to a hydrocarbon chain having from 1 to 20 carbon atoms or an alkyl radical interrupted by at least one oxy or amino group, wherein said radical can also be replaced once or more by halogen, cyano, nitro, amino, monoalkylamino, dialkylamino, alkoxy, hydroxy, aryl and/or epoxy, preferably an epoxy of the general formula (III):

(III)

The silanization reagent is preferably 3-glycidoxypropyltrimethoxy silane. The ratio of silane to silica solid phase may be adjusted to yield matrices with differing densities of silane ligands attached to the solid phase surface.

The silanization reagent may be added directly to the silica solid phase to react therewith. However, the silanization reagent is preferably dissolved in an organic solvent, such as toluene prior to addition to and reaction with the silica solid phase. The silanization reaction can take place at any temperature at which the silanization reagent is stable and reactive with the silica solid phase. The reaction is preferably conducted by incubation of the reagent/solid phase mixture at room temperature for at least four hours, more preferably for at least six hours.

Each of the plurality of silane ligands attached to the silica solid phase in the silanized silica matrix used in the method and kit of the present invention, produced as described above, has a structure encompassed by general formula (I), above. The most referred form of the ligand attached to the silica solid phase of the silanized silica matrix as the structure of general formula (IV):

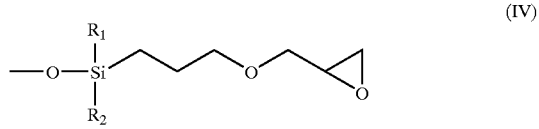

(IV)

wherein, $R_1$ and $R_2$ are each independently —OH, —$CH_3$, —$OCH_3$, —$OCH_2CH_3$, or a linkage to another silane ligand to generate a higher order polymer.

The solid phase matrix of the present invention is designed for use in the isolation of target nucleic acids. Both the ligand configuration, described above, and ligand density can be adjusted to ensure optimal adsorption and desorption of a given target nucleic acid. See Example 8, below, for an example wherein silanated silica magnetic particles with varying ligand densities were used to isolate DNA fragments of varying lengths to identify the solid phase with a suitable ligand density to isolate short DNA fragments (i.e. less than 150 base pairs in length).

The following, non-limiting examples teach various embodiments of the invention. In the examples, and elsewhere in the specification and claims, volumes and concentrations are at room temperature unless specified otherwise. The magnetic silica particles used in the examples below were all porous MagneSil™ particles having the general preferred dimensions and siliceous oxide coating described herein, and modified as described in Example 3, below. The porous MagneSil™ particles used in the Examples below were taken from either of two batches of particles having the following characteristics: (1) a BET surface area of 55 $m^2/g$, pore volume of 0.181 ml/g for particles of <600 Å diameter, pore volume of 0.163 ml/g for particles of >600 Å diameter, median particle size of 5.31 µm, and iron leach of 2.8 ppm when assayed as described herein above using ICP; or (2) a BET surface area of 49 $m^2/g$, pore volume of 0.160 ml/g (<600 Å diameter), pore volume of 0.163 ml/g (>600 Å diameter), median particle size of 5.5 µm, and iron leach of 2.0 ppm.

One skilled in the art of the present invention will be able to use the teachings of the present disclosure to select matrices suitable for use in the method and in the kit of the present invention other than the specific embodiment of the silanized silica magnetic particles produced as described in Example 3, below, and used in the following Examples. Specifically, the Examples should not be construed as limiting the scope of the present invention. Other modified silica magnetic particles, and methods of using the same to isolate target material according to the present invention will be apparent to those skilled in the art of chromatographic separations and molecular biology.

EXAMPLES

The following examples are given to illustrate various aspects of the invention, without limiting the scope thereof:

Example 1

Gel Electrophoresis

Samples of target nucleic acids isolated according to procedures described in Examples below were analyzed for contamination with non-target nucleic acids, and for size as follows. The samples were fractionated on an agarose gel of appropriate density (e.g., a 1.0% agarose gel was used to analyze plasmid DNA, while a 4.0% agarose gel was used to analyze RNA). The fractionated nucleic acid was detected by staining the gel with a nucleic acid sensitive stain, such as ethidium bromide. The resulting fractionated stained gel was photographed.

In some cases, size standards were fractionated on the same gel as the target nucleic acid, and used to determine the approximate size of the target nucleic acid. In every case where a gel assay was done, the photograph of the fractionated nucleic acid was inspected for contamination by non-target nucleic acids. For example, images of fractionated samples of plasmid DNA were inspected for RNA, which runs considerably faster than DNA on the same gel, and for chromosomal DNA, which runs considerably slower than plasmid DNA on the same gel. Images of isolated plasmid DNA were also inspected to determine whether most of the plasmid DNA shown in the image is intact, supercoiled plasmid DNA.

Example 2

Absorption Spectrophotometry

Samples of target nucleic acids isolated from various media, as described below, were also analyzed using absorption spectrophotometry. Absorption measurements were taken at wavelengths of 260, 280, and 230 nanometers (nm). $A_{260}/A_{280}$ absorption ratios were computed from the measurements. An $A_{260}/A_{280}$ of greater than or equal to 1.70 was interpreted to indicate the sample analyzed therein was relatively free of protein contamination. The concentration of nucleic acid in each sample was determined from the absorption reading at 260 nm ($A_{260}$). An $A_{260}$ of 1.0 indicates 50 µg/ml double stranded DNA. Contaminants containing peptide bonds or aromatic moieties such as protein and phenol absorb at 230 nm.

Example 3

Preparation of Glycidyl-Modified Magnesil™ Particles

MagneSil™ particles (Promega) were dried from a water suspension by filtering, rinsing with acetone, then drying in a fume hood at room temperature overnight, followed by drying at 60–70° C. under vacuum for at least 2 hours. The particles were stored in a dessicator until used in silanization reaction.

1. 5 g of the MagneSil™ particles were suspended in 200 ml toluene in a flask equipped with a motorized stirrer.

2. 15 ml of 3-glycidoxypropyltrimethoxy silane was dissolved in 100 ml toluene and added to the reaction flask.

3. The reaction was stirred at room temperature for approximately 6 hours without refluxing, except as provided in the Examples, below.

4. Particles were washed at least three times in toluene used in step 2, above, separating the particles from the solvent each time in a magnetic field. The same particles were also washed at least twice in acetone, in the same manner.

5. After the final washing step, the particle suspension was filtered, dried in a fume hood at room temperature, then further dried under vacuum at 60–70° C.

A sample of the dried particles submitted for elemental analysis was consistent with silanized silica magnetic particles having the structure of general formula (VI), below. The wavy line in the formula below, represents the surface of a MagneSil™ particle.

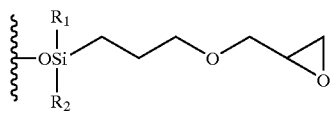

wherein, $R_1$ and $R_2$ are each independently —OH, —CH$_3$, —OCH$_3$, —OCH$_2$CH$_3$ or a linkage to another silane ligand to generate a higher order polymer. The silanized MagneSil™ particles produced as described above are referred to hereinafter as "glycidyl-MagneSil particles". The glycidyl-MagneSil particles were used in the Examples below.

Example 4
Preparation of a Lysate of Plasmid DNA

*E. coli* bacteria cells, DH5α strain, were transformed with pGEM®-3zf⁺ plasmid DNA (Promega), grown overnight in Luria Broth ("LB") medium at 37° C., then harvested by centrifugation.

The following solutions were used to prepare a lysate of the harvested cells, as described below:

Cell Resuspension Solution:
50 mM Tris-HCl, pH 7.5
10 mM EDTA
100 μg/ml DNase-free ribonuclease A (RNase A)

Neutralization Solution, pH 4.2
0.5 K⁺
4.2M GTC (guanidine thiocyanate)
1.9M OAc⁻

Cell Lysis Solution:
0.2M NaOH
1% SDS (sodium dodecyl sulfate)

A lysate of the transformed cells was produced as follows:
1. The cells from 1 to 10 ml of bacteria culture were harvested by centrifuging the culture for 1–2 minutes at top speed in a microcentrifuge. The harvested cells were resuspended in 250 μl of Cell Resuspension Solution, and transferred to a microcentrifuge tube. The resulting solution of resuspended cells was cloudy.
2. 250 μl of Cell Lysis Solution was then added to the solution of resuspended cells and mixed by inversion until the solution became relatively clear, indicating the resuspended cells had lysed.
3. 350 μl of Neutralization Solution was added to the resulting lysate and mixed. The lysate became cloudy after the Neutralization Solution was added.

Each sample of lysate prepared as described above was cleared, by centrifugation or by using MagneSil™ particles or glycidyl-MagneSil particles, as described below.

Example 5
Comparison of Lysate Clearing and Plasmid DNA Isolation with Glycidyl-Magnesil Particles vs. with Magnesil™ Particles with and without Isopropanol A. Lysate Clearance and Isolation of DNA 100 ml overnight culture of DH5α cells transformed with pGEM®-3zf⁺ (Promega) was aliquoted into each of 36 different tubes, harvested by centrifugation, and treated as described in Example 4, above to produce a lysate thereof. The resulting lysate was cleared using one of the following three methods. Lysates from one set of 12 tubes was cleared by centrifugation for ten minutes at 16,000×g, and by removal into a separate, clean, tube. Lysates from another set of 12 tubes were cleared using 5 mg of MagneSil™ particles (50 μl of 100 mg/ml). The lysate solutions from the final set of 12 tubes were cleared using 5 mg of glycidyl-MagneSil. In each case where magnetic particles were used, the particles were allowed to adsorb to material, such as lipids, proteins, and cellular debris in each tube, drawn to one side of the tube by magnetic force, and the remaining cleared lysate removed to a clean tube.

Each set of 12 samples was divided into three subsets of four (4) samples each. The following types of paramagnetic particles and solutions were added to the first set of samples to adsorb to plasmid DNA contained therein: (a) MacneSil™ particles (100 μl of 100 mg/ml) were added to the first of each set of four samples, without isopropanol, (b) MagneSil™ particles (100 μl of 100 mg/ml) were added to the second set of four samples, along with 600 μl of isopropanol per sample, and (c) glycidyl-MagneSil particles were added to the third set of four samples, with 600 μl of isopropanol per sample. All samples were mixed periodically and incubated at 20° C. for 10 minutes.

The particles were separated from each solution using magnetic force, and the supernatants removed and discarded.

Each set of particles was washed three times with 1.0 ml of a Wash Solution (80% ethanol, 20% nanopure water, volume/volume). After the third wash, the particles were air dried at 20° C. for 20 minutes.

Finally, 100 μl of an Elution Solution (200 mM TrisHCl pH 9.5) was added to each sample. The particles plus Elution Solution were incubated at 65° C., uncapped, for 5 minutes. At the end of the incubation period, 10 μl of nanopure water was added to each tube to bring the total volume of solution in each tube back up to 100 μl. All the tubes were centrifuged for 5 minutes at 16,000×g, and the supernatants transferred to clean tubes for analysis, as described below.

B. Assay of Results

A sample of each of the eluents produced as described above was assayed by gel electrophoresis, as described in Example 1, above. DNA ladders were run in two lanes of the gel to confirm that the size of the bands of eluent DNA corresponded to the size expected for the subject plasmid DNA. The gel electrophoresis assay results are shown in FIG. 1. The expected size was confirmed. Intact plasmid DNA was detected in each sample, with no evidence of degradation or RNA contamination in any of the samples. The order in which each of the samples was loaded on the gel is shown in Table 1, below:

TABLE I

| LANES | CLEARED WITH | ISOLATED WITH |
|---|---|---|
| 1 | | Kilobase Ladder (Promega) |
| 2–5 | centrifugation | MagneSil ™ |
| 6–9 | centrifugation | Magnesil ™ + isopropanol |
| 10–13 | centrifugation | glycidyl-MagneSil ™ |
| 14 | | Kilobase Ladder |
| 15–18 | MagneSil ™ | MagneSil ™ |
| 19–20 | MagneSil ™ | MagneSil ™ + isopropanol |
| 21–24 | MagneSil ™ | glycidyl-MagneSil |
| 25 | | Kilobase Ladder (faint) |
| 26–29 | glycidy-MagneSil | MagneSil ™ |
| 30–33 | glycidyl-MagneSil | MagneSil ™ + isopropanol |
| 34–37 | glycidyl-MagneSil | glycidyl-MagneSil |

The amount of DNA in all the samples produced by clearing a lysate with MagneSil™ particles was considerably less than the amount of DNA produced by clearing with glycidyl-MagneSil particles, no matter which of the three protocols tested was used to isolate plasmid DNA from the cleared lysates produced thereby. The amount and quality of DNA appeared to be comparable within each set of twelve cleared lysate samples tested, regardless of the method used to isolate DNA therefrom. Specifically, the gel assay results showed that all the plasmid DNA appeared to be intact and free of contamination.

A spectrophotometric assay was also conducted, as described in Example 2, on all the eluent samples produced as described in Section A, immediately above. The each spectrophotometric scan was performed on 20 μl of each eluent diluted with 380 μl of 200 mM TrisHCl, pH 9.5 in a 400 μl cuvette. The average of the readings from each set of four samples described above is shown in Table II, below:

TABLE II

| SAMPLES | CLEARED WITH | ISOLATED WITH | $A_{260}$ | $A_{280}$ | $A_{260}/A_{280}$ |
|---|---|---|---|---|---|
| 1–4 | centrifugation | MagneSil ™ | 0.247 | 0.135 | 1.83 |
| 5–8 | centrifugation | MagneSil ™ + isoprop. | 0.347 | 0.186 | 1.86 |
| 9–12 | centrifugation | glycidyl-MagneSil | 0.331 | 0.174 | 1.90 |
| 13–16 | MagneSil ™ | MagneSil ™ | 0.0977 | 0.0590 | 1.66 |
| 17–20 | MagneSil ™ | MagneSil ™ + isoprop. | 0.179 | 0.100 | 1.79 |
| 21–24 | MagneSil ™ | glycidyl-MagneSil | 0.104 | 0.0562 | 1.85 |
| 25–28 | glycidyl-MagneSil | MagneSil ™ | 0.270 | 0.151 | 1.79 |
| 29–32 | glycidyl-MagneSil | MagneSil ™ + isoprop. | 0.345 | 0.189 | 1.83 |
| 33–36 | glycidyl-MagneSil | glycidyl-MagneSil | 0.334 | 0.180 | 1.86 |

The yield of DNA isolated from lysates cleared using glycidyl-MagneSil particles was comparable to the yield of DNA of lysates cleared with centrifugation, as shown by the $A_{260}$ readings in Table II. The yield of DNA isolated from lysates cleared with MagneSil™ particles was significantly lower than that obtained using either of the other lysate clearance method tested.

The spectrophotometric assay results in Table II, above, also show that when the same method was used to clear three sets of samples of lysates, and DNA isolated therefrom using the three different isolation methods described above, the amount of DNA isolated from each sample in the set was comparable regardless of which isolation method was used. The purity of all DNA samples isolated above appeared to be high, except for that of the samples cleared and isolated with MagneSil™ particles without isopropanol (samples 13–16). Except for those particular samples, all had $A_{260}/A_{280}$ ratios of at least 1.75, indicating high purity. However, in every set of samples processed using the same lysate clearance method, DNA isolated using glycidyl-MagneSil particles (with isopropanol added) had the highest purity, with DNA isolated using MagneSil™ particles with the same added isopropanol having the next highest purity, and DNA isolated with MagneSil™ particles with no isopropanol added having the lowest purity of the three methods, as determined by $A_{260}/A_{280}$ ratios.

The spectrophotometric results were consistent with the results obtained in the gel assay, described above.

Example 6
Preparation of a Lysate of Sunflower Seeds, and DNA Purified Therefrom Fresh sunflower seeds were hulled, and the seeds were separately lysed in a solution comprising about 1M of chaotropic salt, consisting of (per sample): 250 μl of Wizard® Genomic Nuclei Lysis solution (Promega Cat. No. A7943)+500 μl of (4M GTC, 0.01 M Tris-HCl, pH 7.5)+5 μl of RNase A mixed with a steel bead in a Retsch (Hann, Germany) mixer twice, for two minutes each mixing cycle.

Four seeds were processed in this manner, two of them also had 100 mg of polyvinylpolypyrrolidone (hereafter PVPP) (Sigma P-6755, St. Louis, Mo.) added prior to their mixing in the Retsch mixer. The other two did not contain PVPP.

One sample with PVPP and one sample without PVPP were centrifuged 10 minutes at 16,000×g to clear the lysate. The other sample with PVPP and the other sample without PVPP were each mixed with 20 μl (2 mg) of glycidyl-MagneSil particles and the debris and particles were pulled to one side of the tube using magnetic force.

The supernatants from the four samples were removed to clean 1.5 ml tubes containing 25 μl (2.5 mg) of MagneSil™ particles, and incubated 10 minutes to allow DNA to bind to the MagneSil™ particles. The supernatants were then removed and the particles washed three times with a wash solution containing 1 ml of 25% isopropanol, 25% ethanol, 0.2M NaCl and 10 mM EDTA, with supernatants removed after each wash. The particles were dried at 20° C. for 20 minutes, and eluted in 100 μl of 10 mM Tris HCl, 1 mM EDTA pH 8.0.

Figure 2:
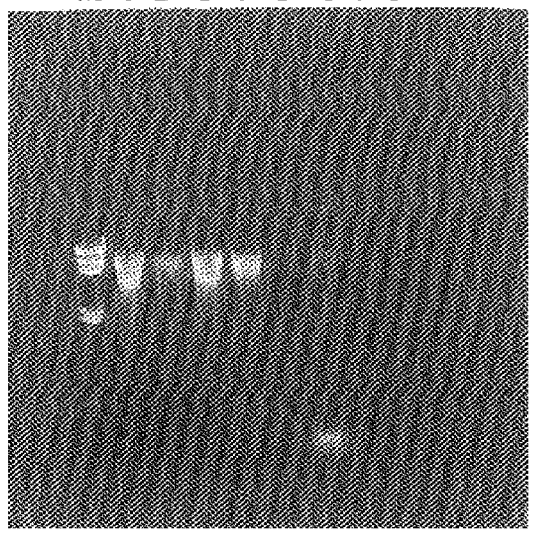
FIG. 2 is a photograph of DNA isolated from sunflower seeds using various means described in Example 6, below, after fractionation on an agarose gel by gel electrophoresis.

10 μl of each eluent sample was loaded on an agarose gel and separated by gel electrophoresis. A photograph of the resulting gel, stained with ethidium bromide is shown in FIG. 2. The gel assay results show that similar DNA yields were obtained with centrifugation and with magnetic clearing using glycidyl-MagneSil particles. The samples containing PVPP showed reduced yields, but the yield using glycidyl-MagneSil particles for clearing was higher than the yield from the samples cleared with centrifugation.

All four samples showed good amplification in PCR (polymerase chain reaction) and RAPD (Random Amplified Polymorphic DNA, see U.S. Pat. No. 5,126,239).

Example 7
Isolation of DNA from Corn Oil

Samples of corn oil from a local supermarket were evaluated for DNA content and a bottle containing visually discernable DNA was used for this example (not all bottles contained enough DNA to visualize with an ethidium bromide stained 4% agarose gel). While the method described below will purify DNA from these other oil samples, the results are not as readily visualized.

Four tubes containing 20 ml of corn oil each had the following solutions added per tube: 200 μl of Wizard® Genomic Nuclei Lysis Solution+100 μl SV Total RNA Lysis Solution+200 μl of SV Total RNA Dilution Solution (See Example 6 for lysis solution compositions). The tubes were vigorously mixed several times during a 20 minute incubation at room temperature. The tubes were then centrifuged for 5 minutes at 3,000×g, and the lower, aqueous phases were removed to clean tubes. Two of these tubes were pooled to obtain samples of the extracted material. Of the remaining two tubes, one sample had 100 μl of MagneSil™ particles added, and another 100 μl of glycidyl-MagneSil particles.

Each of these tubes had 50 μl of 1.32M potassium acetate, pH 4.8, added. 400 μl of isopropanol was then added to each tube; and the tubes were mixed by periodic vortexing during a 20 minute incubation at room temperature.

The tubes were then placed on a magnetic rack for 5 minutes and the supernatants removed. The particles were resuspended in 1.0 ml of nanopure water, and the supernatants removed. This water wash was repeated twice, for a total of 3 washes. The DNA was then eluted in 50 µl of 200 mM Tris HCl pH 9.5.

When the eluents were analyzed by gel electrophoresis, as described in Example 1, it was found that DNA was isolated from corn oil using glycidyl-MagneSil particles. However, no amount of DNA was detected in the sample processed using MagneSil™ particles.

Example 8
Purification of DNA Using Glycidyl-Magnesil Particles

Figure 3A:
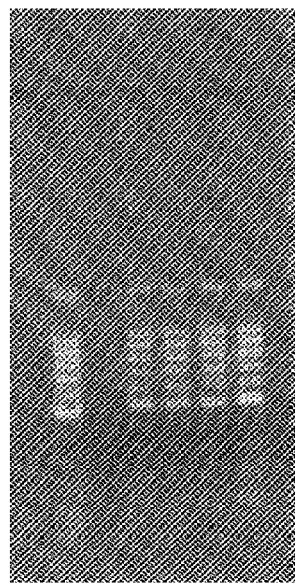
FIG. 3A is a photograph of a nucleic acid adsorption solution containing a DNA ladder, after adsorption of the DNA to glycidyl-modified silica magnetic particles, and fractionation on an agarose gel by gel electrophoresis, as described in Example 8.

DNA of varying lengths was bound to and eluted from glycidyl-MagneSil particles. 50 µl (5 mg) of glycidyl-modified MagneSil™ particles with varying ligand densities were added to 30 µl of Promega's 100 bp DNA ladder (cat #G6951). 30 µl of 66 mM KOAc pH 4.8, was added to the resulting mixture, mixed by vortexing, and incubated 20 minutes at room temperature. After incubation, as described in Example 1, the particles were separated from the solution in a magnetic field, and aliquots of the solution removed therefrom, 11 µl of each of the aliquots was electrophoresed next to a 3 µl sample of the 100 bp ladder. FIG. 3A is a photograph of the gel electrophoresis results, showing that DNA remained in solution, unbound to the glycidyl-modified MagneSil™ particles with lower ligand densities (lanes 3–6). However, no unbound DNA was found in the high ligand density, glycidyl-MagneSil particles prepared as described in Example 3, above.

Figure 3B:
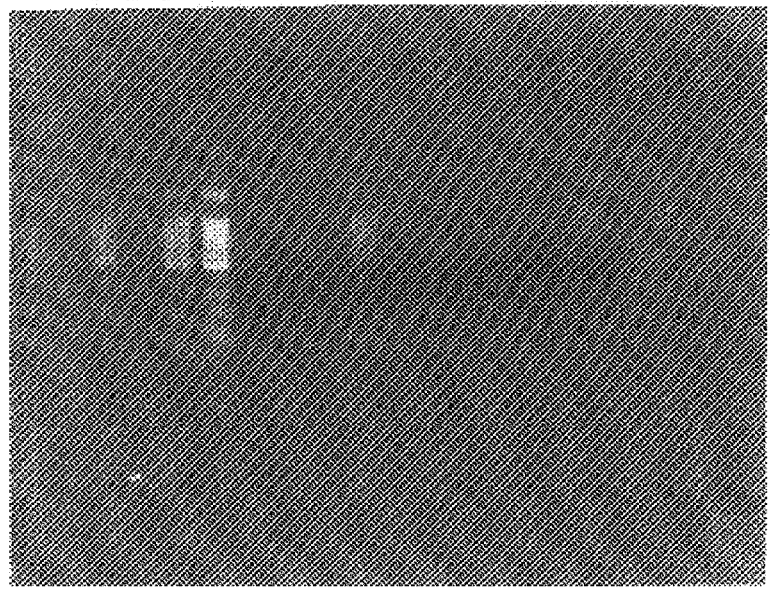
FIG. 3B is a photograph of DNA fractionated by gel electrophoresis, after elution from various glycidyl-modified silica magnetic particles, as described in Example 8.

The solution was then removed from each tube, and the particles were washed twice wish 2.0 ml of nanopure water. The DNA was eluted in 50 µl of 10 mM Tris HCl pH 8.0 for 5 minutes at room temperature, and after magnetic separation, 10 µl of the eluted solution was electrophoresed, next to a sample of 10 µl of elution solution obtained by mixing the glycidyl-MagneSil particles into solution by brief vortexing. This was compared to a 3 µl sample of the Promega 100 bp DNA ladder solution. FIG. 3B is a photograph of the gel electrophoresis results showing that DNA remained on the high ligand density glycidyl-MagneSil particles during the water washes (lane 3), and that the lower molecular weight bands (e.g. 100 bp) were purified with a similar efficiency as the larger (e.g. 600 bp) DNA fragments. Lane 4 of the gel is an aliquot of the glycidyl-MagneSil particles electrophoresed after elution. Lane 1 of the gel is the DNA ladder. The amount of DNA bound to and eluted from the remaining glycidyl-modified MagneSil™ particles significantly decreased with decreasing ligand density.

Example 9
Purification of DNA from Agarose Gel Slices Using Glycidyl-Magnesil Particles and Magnesil™ Particles Promega's 25 bp DNA ladder (catalog #G4511) was run on a 1% agarose gel (BioWhittaker Molecular Applications, Rockland, Me.) for 20 minutes at 200V and the agarose gel slices containing the DNA were excised from the gel. The gel slices weighed 3.7 gm, and were combined in a 50 ml tube with 3.7 ml of 4.2M guanidine thiocyanate, 0.5M potassium, 1.9M acetate, pH 4.2. The tube was incubated for 30 minutes at 60° C., until all gel fragments were dissolved.

500 µl samples of the resulting melted gel slice solution were added to 1.5 ml tubes containing either 50 µl (5 mg) of glycidyl-MagneSil or 50 µl (5 mg) of MagneSil™ particles. Two samples of each particle had no isopropanol (IPA) added, and four samples of each type of particle had 500 µl of IPA added (for a total of 12 samples). These tubes were incubated for 20 minutes at 20° C. to allow DNA to bind to the particles, and the tubes placed into a magnetic separation rack for 5 minutes.

The solutions were then removed from the tubes. The tubes were then washed with either water (2 times with 1.0 ml per wash step) or 80% ethanol (3 times with 1.0 ml per wash step) as described below. After washing, the ethanol washed particles were dried at room temperature for 20 minutes.

The dried particles were combined with 30 µl of 200 mM Tris HCl pH 9.5 to elute DNA adsorbed thereto. 10 µl of each eluent sample was loaded on a 4% agarose gel and fractioned by gel electrophoresis, as described in Example 1.

Figure 4:
FIG. 4 is a photograph of DNA isolated from an agarose gel silica, as described in Example 9, alter fractionation by gel electrophoresis.

FIG. 4 is a photograph of the electrophoresis gel produced as described above. Table III shows which samples were loaded in the top lanes of the gel in FIG. 4. Table IV shows the samples loaded in each of the lanes of the bottom half of the gel in FIG. 4.

TABLE IV

| Lane | Adsorption Conditions | Wash Conditions |
|------|----------------------|-----------------|
| 1 | DNA ladder | None |
| 2 | No sample | None |
| 3 | DNA ladder | None |
| 4 | No sample | None |
| 5 | glycidyl-MagneSil ™ + IPA | Water |
| 6 | glycidyl-MagneSil ™ + IPA | Water |
| 7 | No sample | None |
| 8 | glycidyl-MagneSil ™ + IPA | Ethanol |
| 9 | glycidyl-MagneSil ™ + IPA | Ethanol |
| 10 | No sample | None |
| 11 | glycidyl-MagneSil ™ no IPA | Water |
| 12 | glycidyl-MagneSil ™ no IPA | ethanol |

TABLE IV (Bottom Wells)

| Lane | Adsorption Conditions | Wash Conditions |
|------|----------------------|-----------------|
| 1 | DNA ladder | None |
| 2 | No sample | None |
| 3 | DNA ladder | None |
| 4 | No sample | None |
| 5 | MagneSil ™ no IPA | Water |
| 6 | MagneSil ™ no IPA | Water |
| 7 | No sample | None |
| 8 | MagneSil ™ no IPA | Ethanol |
| 9 | MagneSil ™ no IPA | Ethanol |
| 10 | No sample | None |
| 11 | MagneSil ™ + IPA | Ethanol |
| 12 | MagneSil ™ + IPA | Ethanol |

As seen FIG. 4, the glycidyl-MagneSil particles bound the lower molecular weight fragments of the 25 bp DNA ladder (the 25 bp fragments were not as easily seen), but the MagneSil™ particles did not bind them as well as the glycidyl-MagneSil, under the conditions tested. Note that the relative recoveries of the 50 bp, 75 bp, 100 bp, and 125 bp fragments were comparable to one another using glycidyl-MagneSil as seen within lanes 5, 6, 8 and 9. The use of glycidyl-MagneSil also allows the recovery of DNA after washing with water under these conditions (acidic pH), which removes the drying step required when using alcohol washes.

What is claimed is:

1. A method of clearing a solution of disrupted biological material, according to steps comprising:
   (a) providing a first silanized silica matrix, comprising a silica solid phase with a plurality of silane ligands covalently attached thereto, wherein each of the plurality of ligands has a neutral charge in a first solution; and
   (b) combining the first silanized silica matrix with the first solution, comprising a disrupted biological material, a target nucelic acid material, and a chaotropic salt at a concentration sufficient to promote selective adsorption or the disrupted biological material to the matrix, thereby forming a first complex between the silanized silica matrix and the disrupted biological material.

2. The method of claim 1, wherein the disrupted biological material is a bacterial cell lysate.

3. The method of claim 1, wherein the disrupted biological material is disrupted plant matter.

4. The method or claim 1, wherein the chaotropic salt concentration in step (b) is at least about 0.5 M.

5. The method of claim 1, wherein the each ligand in the plurality of silane ligands is of the general formula:

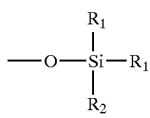

wherein $R_1$ and $R_2$ are each a subunit selected from the group consisting of a hydrocarbon chain having from 1 to 5 carbon atoms, an alkoxy having from 1 to 5 carbon atoms, a halogen atom, a hydrogen atom, a hydroxy, an alkyl chain having from 4 to 10 carbon atoms interrupted by an oxy residue wherein up to five of the carbon atoms is substituted by a group selected from the group consisting of a halogen, an alkoxy having from 1 to 3 carbon atoms, a cyano having from 1 to 3 carbon atoms, a hydroxy, and a linkage to another silane ligand; and wherein $R_3$ is a hydrocarbon chain having from 1 to 20 carbon atoms substituted by at least one hydroxy, an alkyl chain having from 4 to 20 carbon atoms interrupted by at least one oxy group wherein up to ten carbon atoms are replaced by a moiety selected from the group consisting of a halogen, a cyano having from 1 to 3 carbon atoms, an alkoxy having from 1 to 3 carbon atoms, a hydroxy and an epoxy.

6. The method of claim 1, wherein each ligand in the plurality of silane ligands is of the general formula:

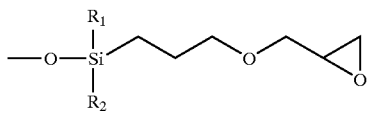

wherein, $R_1$ and $R_2$ are each independently selected from the group consisting of —OH, —$CH_3$, —$OCH_3$, and a linkage to another silane ligand to generate a higher order polymer.

7. The method of claim 1, wherein the silica solid phase is a first silica magnetic particle.

8. The method of claim 1, further comprising a step of separating the first complex from the first solution, thereby producing a cleared solution.

9. The method of claim 8, further comprising a step of combining the cleared solution with a second silica matrix in a second solution, wherein the target nucleic acid specifically adsorbs to the second silica matrix, thereby forming a second complex.

10. The method or claim 9, wherein the second silica matrix comprises a plurality of second silica magnetic particles.

11. The method of claim 9, wherein the second silica matrix is a plurality of second silanized silica magnetic particles, and the second solution has a pH of up to about 8.0.

12. The method of claim 9, wherein the first silica matrix and the second silica matrix are the same.

13. A method of clearing a solution of disrupted biological material, according to steps comprising:
(a) providing a first silanized silica magnetic particle comprising a silica magnetic particle with a plurality of silane ligands covalently attached thereto;
(b) combining the first silanized silica magnetic particle with a first solution, comprising a disrupted biological material, a target nucleic acid, and a chaotropic salt concentration sufficiently high to promote selective adsorption of the disrupted biological material to the silanized silica magnetic particle, thereby forming a first complex between the silanized silica matrix and the disrupted biological material;
(c) separating the first complex from the first solution, thereby forming a cleared solution.

14. The method of claim 13 wherein the disrupted biological material is a bacterial cell lysate.

15. The method of claim 13 wherein the disrupted biological material is disrupted plant matter.

16. The method of claim 13, wherein the first solution further comprises a chaotropic salt at a concentration of up to about 3.5M.

17. The method of claim 13, wherein the each of the plurality of silane ligands is of the general formula:

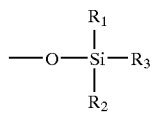

wherein $R_1$ and $R_2$ are each a subunit selected from the group consisting of a hydrocarbon chain having from 1 to 5 carbon atoms, an alkoxy having from 1 to 5 carbon atoms, a halogen atom, a hydrogen atom, a hydroxy, an alkyl chain having from 4 to 10 carbon atoms interrupted by an oxy residue wherein up to five of the carbon atoms is substituted by a group selected from the group consisting of a halogen, an alkoxy having from 1 to 3 carbon atoms, a cyano having from 1 to 3 carbon atoms, and a hydroxy; wherein $R_3$ is a hydrocarbon chain having from 1 to 20 carbon atoms substituted by at least one hydroxy, an alkyl chain having from 4 to 20 carbon atoms interrupted by at least one oxy group wherein up to ten carbon atoms are replaced by a moiety selected from the group consisting of a halogen, a cyano having from 1 to 3 carbon atoms, an alkoxy having from 1 to 3 carbon atoms, a hydroxy, an epoxy, and a linkage to another silane ligand.

18. The method of claim 13, wherein the first complex is separated from the first solution in the presence of a magnetic field.

19. The method of claim 13, wherein the first complex is separated from the first solution by centrifugation.

20. The method of claim 13, further comprising a step of combining the cleared solution with a second silica matrix in a second solution, wherein the target nucleic acid specifically adsorbs to the second silica matrix, thereby forming a second complex.

21. The method of claim 20, wherein the second silica matrix is a second silanized silica magnetic particle comprising a silica magnetic particle solid phase with a plurality of silane ligands covalently attached thereto.

22. The method of claim 21, wherein the first silanized silica magnetic particle and the second silanized silica magnetic particle are the same.

23. The method of claim 20, wherein the second silica matrix is a silica magnetic particle.

24. The method of isolating a target nucleic acid from a nucleic acid adsorption solution, comprising the steps of:

(a) providing a silanized silica matrix comprising a silica solid phase with a plurality of silane ligands covalently attached thereto, wherein each of the plurality of silane ligands is of the general formula:

$$-O-\underset{\underset{R_2}{|}}{\overset{\overset{R_1}{|}}{Si}}-R_1$$

wherein $R_1$ and $R_2$ are each a subunit selected from the group consisting of a hydrocarbon chain having from 1 to 5 carbon atoms, an alkoxy having from 1 to 5 carbon atoms, a halogen atom, a hydrogen atom, a hydroxy, an alkyl chain having from 4 to 10 carbon atoms interrupted by an oxy residue wherein up to five of the carbon atoms is substituted by a group selected from the group consisting of a halogen, an alkoxy having from 1 to 3 carbon atoms, a cyano having from 1 to 3 carbon atoms, and a hydroxy; wherein $R_3$ is a hydrocarbon chain having from 1 to 20 carbon atoms substituted by at least one hydroxy, an alkyl chain having from 4 to 20 carbon atoms interrupted by at least one oxy group wherein up to ten carbon atoms are replaced by a moiety selected from the group consisting of a halogen, a cyano having from 1 to 3 carbon atoms, an alkoxy having from 1 to 3 carbon atoms, a hydroxyl, an epoxy, and a linkage to another silane ligand;

(b) combining the silanized silica matrix with a nucleic acid adsorption solution having a pH of up to about pH 8.0, the nucleic acid adsorption solution comprising the target nucleic acid and at least one non-target material, wherein the target nucleic acid selectively adsorbs to the silanized silica matrix, thereby forming a complex; and (c) separating the complex from the nucleic acid adsorption solution.

25. The method of claim 24, wherein the nucleic acid adsorption solution comprises a vegetable oil.

26. The method of claim 24, wherein the nucleic acid absorption solution further comprises a concentration of low molecular weight alcohol sufficient to promote adsorption of the target nucleic acid to the second silanized silica matrix.

27. The method of claim 24, wherein the adsorption solution further comprises 0.2M to 1.2M of a chaotropic salt.

28. The method of claim 27, wherein the chaotropic salt is selected from the group consisting of guanidine hydrochloride and guanidine thiocyanate.

29. The method of claim 24, wherein the silica solid phase of the silica matrix is a silica magnetic particle.

30. The method of claim 29, wherein the complex is separated from the nucleic acid adsorption solution in the presence of a magnetic field.

31. The method of claim 24, further comprising washing the complex in a wash solution having a pH of up to about 8.0.

32. The method of claim 31, wherein the wash solution comprises a concentration of at least about 30% of a low molecular weight alcohol.

33. The method of claim 24, further comprising combining the complex with an elution solution having a pH of at least about 8.0, thereby desorbing the target nucleic acid from the complex.

34. The method of claim 33, wherein the elution solution is a buffer having a pH of at least about 9.0.

35. The method of claim 24, wherein the target nucleic acid is selected from the group consisting of plasmid DNA, geonomic DNA, and total RNA.

36. The method of claim 24, wherein the target nucleic acid is double-stranded linear DNA with a molecular weight of at least about 25 base pairs and up to about 60 kilobase pairs.

37. A method of isolating a target nucleic acid from a nucleic acid adsorption solution using a silanized magnetic particle, comprising the steps of:

(a) providing a silanized silica magnetic particle, comprising a silica magnetic particle with a plurality of silane ligands covalently attached thereto, wherein each of the plurality of silane ligands is of the general formula:

$$-O-\underset{\underset{R_2}{|}}{\overset{\overset{R_1}{|}}{Si}}-\!\!\!\diagup\!\!\!\diagdown\!\!\!\diagup\!\! O\!\diagdown\!\!\!\diagup\!\!\!\overset{O}{\diagdown\!\!\!\mid}$$

wherein formula, $R_1$ and $R_2$ are each independently selected from the group consisting of —OH, —CH$_3$, —OCH$_3$, or —OCH$_2$CH$_3$ and a linkage to another silane ligand to generate a higher order polymer;

(b) combining the silanized silica magnetic particle with a nucleic acid adsorption solution having a pH of up to about pH 8.0, the nucleic acid adsorption solution comprising the target nucleic acid and at least one non-target material, wherein the target nucleic acid selectively adsorbs to the silanized silica magnetic particle, thereby forming a complex; and (c) separating the complex from the adsorption solution.

38. The method of claim 37, wherein the adsorption solution has a pH of up to about 8.0.

39. The method of claim 37, wherein the adsorption solution comprises a vegetable oil.

40. The method of claim 37, wherein the adsorption solution comprises the target nucleic acid from an agarose gel slice and the agarose gel.

41. The method of claim 37, wherein the adsorption solution further comprises a concentration of low molecular weight alcohol sufficient to promote adsorption of the target nucleic acid to the silanized silica magnetic particle.

42. The method of claim 37, wherein the adsorption solution further comprises a chaotropic salt.

43. The method of claim 42, wherein the chaotropic salt is selected from the group consisting of guanidine hydrochloride and guanidine thiocyanate.

44. The method of claim 37, further comprising washing the complex in a wash solution having a pH of up to about 8.0

45. The method of claim 44, wherein the wash solution comprises a concentration of at least about 30% of low molecular weight alcohol.

46. The method of claim 37, further comprising combining the complex with an elution solution having a pH of at least about 8.0, thereby eluting the target nucleic acid from the complex.

47. The method of claim 37, wherein the target nucleic acid is selected from the group consisting of plasmid DNA, genomic DNA, and total RNA.

48. The method of claim 37, wherein the target nucleic acid is DNA with a molecular weight of at least 25 base pairs and up to about 60 kilobase pairs.

49. A kit comprising, in a single container:

a plurality of silanized silica magnetic particles comprising a silica solid phase with at least one silane ligand covalently attached to the surface of each particle, the silane ligand having a structure of formula:

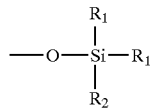

wherein $R_1$ and $R_2$ are each a subunit selected from the group consisting of a hydrocarbon chain having from 1 to 5 carbon atoms, an alkoxy having from 1 to 5 carbon atoms, a halogen atom, a hydrogen atom, a hydroxy, an alkyl chain having from 4 to 10 carbon atoms interrupted by an oxy residue wherein up to five of the carbon atoms is substituted by a group selected from the group consisting of a halogen, an alkoxy having from 1 to 3 carbon atoms, a cyano having from 1 to 3 carbon atoms, and a hydroxy; wherein $R_3$ is a hydrocarbon chain having from 1 to 20 carbon atoms substituted by at least one hydroxy, an alkyl chain having from 4 to 20 carbon atoms interrupted by at least one oxy group wherein up to ten carbon atoms are replaced by a moiety selected from the group consisting of a halogen, a cyano having from 1 to 3 carbon atoms, an alkoxy having from 1 to 3 carbon atoms, a hydroxy, an epoxy, and a linkage to another silane ligand.

50. The method of claim 31, wherein the wash solution is water.

51. The method of claim 44, wherein the wash solution is water.

* * * * *